United States Patent [19]

Mansfield et al.

[11] 4,297,337

[45] Oct. 27, 1981

[54] SOLID-PHASE IMMUNOASSAYS USING MAGNETIC GLASS

[75] Inventors: Gerald R. Mansfield, Painted Post; Karen L. Travis, Corning; William P. Vann, Beaver Dams, all of N.Y.

[73] Assignee: Corning Glass Works, Corning, N.Y.

[21] Appl. No.: 29,576

[22] Filed: Apr. 13, 1979

[51] Int. Cl.$^3$ .................. G01N 33/48; G01T 1/00
[52] U.S. Cl. .................................. 424/1; 424/1.5; 424/12; 23/230 B
[58] Field of Search .................. 23/230 B; 424/1, 1.5, 424/12

[56] References Cited

U.S. PATENT DOCUMENTS

| | | | |
|---|---|---|---|
| 3,555,143 | 1/1971 | Axen et al. | 424/1 |
| 3,652,761 | 3/1972 | Weetall | 424/12 |
| 3,654,090 | 4/1972 | Schuurs et al. | 435/7 |
| 3,933,997 | 1/1976 | Hersh et al. | 424/1 |
| 3,940,475 | 2/1976 | Gross | 424/1 |
| 3,970,518 | 7/1976 | Giaever | 435/7 |
| 3,985,649 | 10/1976 | Eddelman | 366/273 |
| 4,018,886 | 4/1977 | Giaever | 23/230 B X |
| 4,098,876 | 7/1978 | Piassio et al. | 424/1 |
| 4,115,534 | 9/1978 | Ithakissios | 23/230 B X |
| 4,177,253 | 12/1979 | Davies et al. | 23/230 B X |

OTHER PUBLICATIONS

Immobilized Enzymes for Industrial Reactors, R. A. Messing, Ed., Academic Press, NY, 1975, pp. 39–61.
Nye et al., Clin. Chim. Acta, 69, 387 (1976).
Ithakissios et al., Clin. Chim. Acta, 84, 69 (1978).
Ithakissios et al., Clin. Chem., 23, 2072 (1977).

Primary Examiner—Benjamin R. Padgett
Assistant Examiner—Christine M. Nucker
Attorney, Agent, or Firm—Willim E. Maycock

[57] ABSTRACT

Solid-phase immunoassay procedures employing magnetic glass or crystal-containing material, or a superparamagnetic material formed of magnetic particles dispersed in a non-magnetic matrix, as particulate carrier.

34 Claims, 1 Drawing Figure

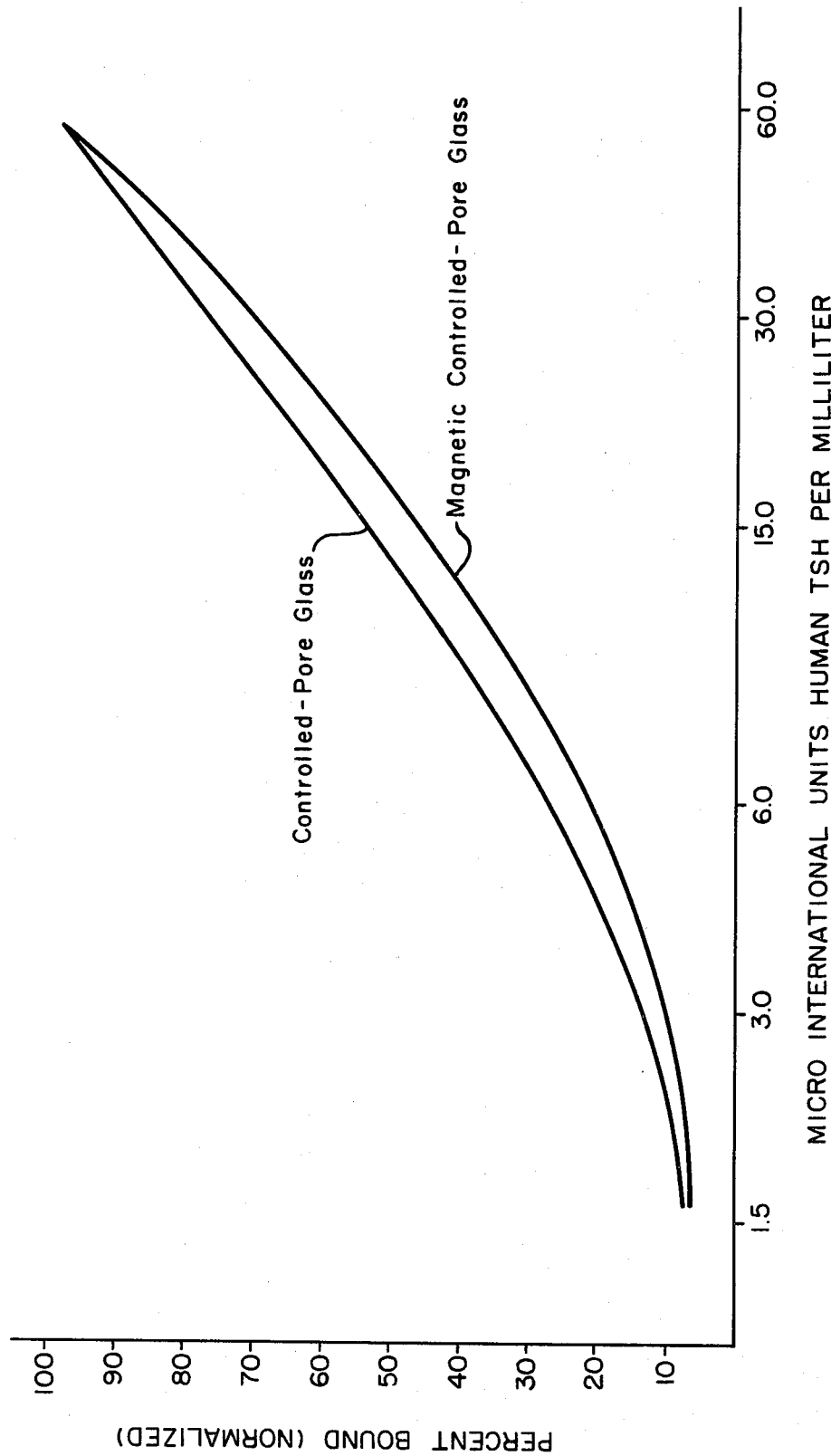

SOLID-PHASE IMMUNOASSAYS USING MAGNETIC GLASS

BACKGROUND OF THE INVENTION

1. Field of the Invention

This disclosure is concerned generally with methods of detecting and/or determining the concentration of various substances found in fluids, especially human body fluids. More specifically, the disclosure is concerned with particulate carriers used in methods of determining such substances via solid-phase immunoassay techniques.

2. Prior Art

The expression "immunoassay", as used herein, refers to a method of determining the presence or concentration of a substance in a fluid, which method is based on the use of antibodies specific to that substance. Since it is known that antibodies to a given substance are extremely specific to that substance, research efforts have been directed in recent years to use that specificity in determining the presence or concentration of substances which are present in very small quantities in fluids, especially human body fluids such as blood. Although there now exists a wide variety of immunoassay techniques, the more common assays require the use of a label for either the antibody or the antigenic substance or hapten being determined. The use of a label permits a relatively rapid detection or quantitation in conventional laboratories using conventional equipment. A variety of labels is known and used in immunoassays. For example, fluorogenic materials useful in a fluoroimmunoassay (FIA) are described in U.S. Pat. No. 3,940,475 to Gross. Enzyme markers can be coupled to antibodies or antigens to perform an enzyme immunoassay (EIA) as illustrated in U.S. Pat. No. 3,654,090 to Schuurs et al. Radioisotopes can be incorporated into an antibody or substance to perform a radioimmunoassay (RIA) as illustrated in U.S. Pat. No. 3,555,143 to Axen et al. As used herein, the expression "labeled antibody" or its equivalent includes any of those known labels.

A typical immunoassay requires, at some point, an immunochemical complexation between an antigenic substance and its respective antibody. Commonly, one of the species in such a complexation is labeled, and, by competing with, complexing with, or displacing an unknown substance in such complexation, and then quantitating the label (e.g., fluorometrically, enzymatically, radiometrically, etc.), it is possible to determine the unknown by known means. Prior to such quantitation, however, it is generally necessary to separate the immunochemically complexed products from the surrounding incubation medium. Such separations can be facilitated by providing one of the species involved in an immobilized, insoluble form. For example, it is known that antigenic substances, haptens or antibodies thereto can be attached to, or incorporated in, various water-insoluble carrier materials without substantial loss of biological activity. See, for example, U.S. Pat. Nos. 3,555,143 (organic carriers) and 3,652,761 (inorganic carriers). When either of the reactants in an immunoassay is used in such an immobilized form, there is present a solid phase which, when appropriate, can be readily separated (e.g., by centrifugation or filtration) for label quantitation. The use of composites comprising antibodies or antigens associated with or immobilized on essentially water-insoluble carrier materials is commonly referred to as a solid-phase immunoassay (SPIA).

As used herein, the expression "immobilized antibody composite" or the equivalent includes all forms of antibodies which have been attached to insoluble materials.

Porous glass is used as the water-insoluble carrier phase in a number of SPIA systems available commercially from Corning Medical, Corning Glass Works, Medfield, Mass.; for example, T-4 (thyroxine) and TSH (thyrotropin) RIA test systems.

The type of porous glass used in the above-identified RIA's is a "controlled-pore glass" formed by leaching a borosilicate glass. See "Controlled-Pore Glasses for Enzyme Immobilization", by Filbert, as Chapter 3 in *Immobilized Enzymes for Industrial Reactors*, Messing (ed.), Academic Press (1975), describing preparation, composition, physical, chemical, and mechanical properties and surface chemistry, including covalent bonding of biologicals to the controlled-pore glass, of such glasses. Although non-porous glass could be employed as a carrier phase, the porous glass offers obvious advantages in providing a high surface area per unit volume.

Solid phase carrier materials are normally used in finely-divided particulate form for two main reasons. Firstly, in order to make assays quantitative, several known concentrations of the species being assayed are measured, along with the samples to be assayed, forming a batch of test samples. By carefully ensuring that all test samples are treated identically, the known concentrations provide a standard or calibration curve for that particular batch. By attaching the reagent to finely-divided particles, which are dispersed in liquid in a gently stirred receptacle, each predetermined volume drawn from the receptacle contains the same quantity of reagent. Secondly, most assays involve an incubation period during which the immobilized reagents react with other reagents in solution. It is desirable that the immobilized reagent remains dispersed in suspension without serious sedimentation so that dissolved reagents do not have to diffuse very far to reach immobilized material. Conversely, the difficulty of centrifuging down very fine particles leads to "fines" being thrown away as undesirable. From these considerations the present practice of using porous glass particles of perhaps 0.5 to 3 microns diameter and 50% to 70% by volume porosity has emerged.

As noted hereinbefore, centrifugation is routinely used to separate the solid phase from the reaction fluid. The fluid is manually or mechanically decanted. Depending upon the centrifuge available, number of samples being assayed, and so on, separation can take up to 10 minutes or more.

Magnetic separation has been considered in the art to avoid the need for centrifugation. In this type of procedure, the water-insoluble solid carrier is a magnetic particle. Then, separation can be carried out in a magnetic field, for example, by "holding" the magnetic particles while the reaction fluid is removed therefrom. U.S. Pat. No. 3,933,997 to Hersh et al. discloses the use of an immunoadsorbent of anti-digoxin antibodies coupled through an intermediate silane to iron oxide particles. Nye et al., Clin. Chim. Acta. 69:387 (1976), describe antibodies covalently linked to polymer-coated iron oxide. Guesdon et al., Immunochem. 14:443 (1977), describe the use of magnetic polyacrylamideagarose-magnetite beads for use in solid-phase enzymeimmunoassay. Ithakissios et al., Clin. Chim. Acta. 84:69 (1978) and Clin. Chem. 23/11,2072 (1979) describe magnetic microparticles of a protein matrix containing magnetic material and use thereof in immunoassays.

U.S. Pat. Nos. 3,970,518 and 4,018,886, both to Giaever, disclose the presence of a monomolecular coating of antibody and protein, respectively, on magnetic particles ranging from colloidal size to about 10 microns to detect biological particles which will specifically interact with the coated material. The Giaever patents contemplate the types of magnetic particles as follows:

Ferromagnetic, ferrimagnetic and superparamagnetic materials are useful in the practice of this invention. Other suitable magnetic materials include oxides, such as, for example, ferrites, perovskites, chromites and magnetoplumbites.

The single example in Giaever U.S. Pat. No. 4,018,886 uses nickel particles about 1 micron in diameter coated with bovine serum albumin. One disadvantage of using such relatively large particles of the magnetic material is that the particles will tend to adhere to one another after removal of the magnetic field because of residual magnetism. Also, pure magnetic material usually has a high density.

U.S. Pat. No. 3,985,649 to Eddelman describes ferromagnetic particles of (1) a ferromagnetic core coated with a biomaterial support such as glass, or porous glass, (2) ferromagnetic particles adhesively attached to the biomaterial support or (3) blending a very finely divided ferromagnetic substance with a support material such as a polymer, and then forming the ferromagnetic particles. A biologically active material can be affixed to the ferromagnetic particles for use in RIA techniques.

Those skilled in the art will recognize that the force on a suspended magnetic particle subjected to a magnetic field is directed to move the particle to stronger field regions (typically towards the pole of a magnet) and that the strength of the force depends both on the field gradient and magnetism induced in the particle by the field. Thus, for rapid separation, a strong separator and a highly magnetizable particle appear preferable.

SUMMARY OF THE INVENTION

It is an object of this invention to provide an SPIA water-insoluble carrier material which has the attributes, such as surface area and chemical inertness, of controlled-pore glass carriers but does not require centrifugation or filtration for separation from a reaction fluid.

It is another object of this invention to provide SPIA test procedures in which the immunochemically-complexed products are separated from the reaction fluid by magnetic separation.

Another object of this invention is to provide magnetically-dilute particles which can be separated effectively by a relatively weak magnetic separator.

A further object of this invention is to provide water-insoluble magnetic particles, useful as a solid phase in SPIA, which do not stick to one another upon removal of a magnetic field.

Still another object of this invention is to provide an antigen, hapten or antibody complexed with a water-insoluble magnetic carrier material.

Other objects of this invention will be apparent to the skilled artisan from the Detailed Description of the Invention hereinafter.

In accordance with the above objectives, it has now been found that magnetically-dilute particles of magnetic glass can be used as the water-insoluble, solid-phase carrier material in SPIA test procedures.

In a preferred embodiment of this invention, the magnetic glass is a porous magnetic glass or crystal-containing material providing high surface area.

In another preferred embodiment of this invention, the magnetic glass or crystal-containing material is substantially superparamagnetic.

In the most preferred embodiment of this invention, the magnetic glass or crystal-containing material is both porous and superparamagnetic.

In another embodiment of this invention directed to the use of magnetically-dilute particles, preferably substantially superparamagnetic particles, a matrix other than glass is used. The principal properties demanded in such matrix materials are that they be water-insoluble, durable, and inert to the testing procedure. For example, organic plastics, glass-ceramics, and other predominantly crystalline ceramics can be used as the matrix in this embodiment.

By magnetic glass is meant glass particles of the usual size used in SPIA procedures containing therein sufficient magnetic material so that the glass particle acts as a magnetic particle, that is, it responds to a magnetic field.

The production of porous magnetic glass or crystal-containing particles constituting the preferred carrier material in the present invention is described in U.S. application Ser. No. 29,577, filed concurrently herewith in the names of G. H. Beall, G. R. Mansfield and J. W. H. Schreurs, and now U.S. Pat. No. 4,233,169, the disclosure thereof being incorporated herein by reference. Those products have magnetic particles incorporated therein with dimensions of less than about 1000 Å, preferably less than 500 Å, which are essentially enveloped within the glass and/or crystal structure.

The preparation of such porous bodies is founded in glass compositions which, upon heat treatment, separate into at least two chemically-distinct, co-connected vitreous phases of different solubility. Such glasses, after heat treatment at elevated temperatures, i.e., ranging from about the transformation of the glass up to but below the miscibility temperature of the two phases, to cause separation of the two vitreous phases, are subjected to various etchants which preferentially remove the more soluble phase. It is this removal of the more soluble phase which provides articles having interconnected or continuous pores.

The glass compositions most widely-recognized in the prior art as demonstrating this phenomenon are found in the borosilicate system. Thus, upon heat treatment, such glasses separate into a silica-rich phase and a borate-rich phase. The latter is quite highly soluble in a number of mineral acids whereas the former phase is not.

It was also observed in that application that, during the heat treatment causing the phase separation to occur, crystals may develop in the body. In point of fact, the inventive method relies upon the growth of iron-containing crystals to impart magnetic character to the final product. However, the generation of crystals other than iron-containing phases may also take place simultaneously with the separation of the vitreous phases. Such products may range from predominantly glasses, i.e., bodies containing but a relatively few crystals other than iron-containing phases, to predominantly crystalline glass-ceramics. It is possible that such crystals may incorporate therewithin a portion of an iron-containing phase.

As utilized in that application, "crystal-containing materials" encompass products prepared via the phase separation of glass and containing more than trace amounts of crystals in addition to iron-containing phases. The term "glass material" refers to those products consisting essentially solely of a vitreous structure having iron-containing crystals enveloped therewithin.

The preferred base compositions operable in that invention lie in the alkali metal oxide, iron oxide, boron oxide, silica system with the most preferred compositions consisting essentially, expressed in weight percent on the oxide basis, of about 3–15% $Na_2O$ and/or $K_2O$, 10–25% $Fe_2O_3$, 10–40% $B_2O_3$, and 35–70% $SiO_2$. Porous glass bodies prepared from such compositions consist essentially of a vitreous silica structure with magnetic crystals enveloped therewithin. The magnetic crystals will customarily consist of magnetite ($Fe_3O_4$) and/or solid solutions of magnetite with $\gamma$-$Fe_2O_3$. Where various modifying oxides such as CoO, NiO, MnO, and ZnO are optionally included in the composition, ferrite solid solutions may also be developed during the heat treatment step. Porous crystal-containing materials prepared from the above compositions consist essentially of a glassy-crystalline skeleton with magnetic crystals enveloped therewithin. The glass consists essentially of vitreous silica and the crystal phase consists essentially of a silica-containing species. Again, the magnetic crystals will be magnetite and/or solid solutions of magnetite with $\gamma$-$Fe_2O_3$ and/or other ferrite solid solutions having crystal structures similar to that of magnetite.

The definitions of "glass material" and "crystal-containing material" utilized in that application will also be employed here. It will be appreciated that, where a non-porous carrier is desired, the leaching step can be omitted. However, for the most favorable inertness and insolubility, essentially non-leachable compositions and/or compositions which do not phase separate upon heat treatment, e.g., compositions not in the alkali metal-iron-borosilicate system, may well be better than non-leached bodies of leachable glasses or crystal-containing materials. Hence, water and other liquids utilized in assay techniques may rapidly attack somewhat leachable materials.

BRIEF DESCRIPTION OF THE DRAWING

The appended drawing is a graph which compares a standard dose response curve in a thyroid stimulating hormone (TSH) assay obtained using controlled-pore glass with the standard dose response curve generated from essentially the same assay procedure, but substituting controlled-pore superparamagnetic glass prepared in accordance with Ser. No. 29,577 (now U.S. Pat. No. 4,233,169) above as the solid-phase carrier. Centrifugal separation was used in both instances to prepare the curves. The similar curves show that the glasses are functionally equivalent in the protein bonding assay. Other tests have shown that magnetic separation in a weak magnetic separator is practical with the magnetic glass.

DETAILED DESCRIPTION OF THE INVENTION

The present invention is believed applicable to substantially all SPIA procedures. As long as a particulate, inert, water-insoluble carrier is employed, the magnetic particles of the present invention can simply be substituted into the known testing procedure. For example, Corning Medical makes available commercially a series of IMMO PHASE ™ kits using controlled-pore glass as the carrier. As examples only, there are RIA-type IMMO PHASE ™ kits for quantitatively determining T-4 (thyroxine) in serum, Free-T-4 (the fraction of T-4 not bound to a transport protein), and TSH (thyrotropin or thyroid stimulating hormone) which use controlled-pore glass carriers. In each of these procedures, one may employ the magnetic particles of the present invention in place of the controlled-pore glass of the RIA kit. In addition to RIA procedures, enzyme and fluorogenic material-based SPIA's are known and these can be used with the carriers of the present invention, see U.S. Pat. No. 3,654,090 with respect to enzyme labeling and U.S. Pat. No. 3,940,475 directed to fluoroimmunoassay. For example, fluoroimmunoassay of human immunoglobulin can be carried out using an SPIA procedure with the carrier of this invention.

In its broadest aspect, the magnetic particulate carrier of this invention consists essentially of magnetically-dilute material comprised of a non-magnetic matrix containing finely-divided magnetic material dispersed therein. In a preferred aspect of the invention, the magnetic carrier is substantially superparamagnetic.

By "magnetically-dilute" material is meant that the magnetic substances are diluted by the inert, non-magnetic matrix. Also, as used herein, "substantially superparamagnetic" refers to magnetic particles which are characterized by having no substantial residual magnetism upon completion of a magnetization-demagnetization cycle (hysteresis loop), or having such a low residual magnetism that the individual magnetic particles will not stick to one another after removal of a magnetic field. In this manner, agglomeration which would normally be expected to persist after a suspension of magnetic particles has been subject to a magnetic field is substantially eliminated.

One way to obtain a superparamagnetic carrier particle is to disperse very fine particles of a magnetic material throughout a non-magnetic matrix. It is believed that superparamagnetism will be found where the dispersed magnetic material or crystallites is of a size up to about 175 Å, say 100–175 Å, in diameter. However, residual magnetism is so low with dispersed particles up to about 500 Å in size that the practical effect of superparamagnetism is still obtained; that is, agglomeration of the magnetic carrier particles does not persist after removal of a magnetic field. The above size range is believed suitable for crystals with structures similar to magnetite and the critical size of dispersed particles may vary somewhat depending upon the particular magnetic material used. Of course, other procedures for producing superparamagnetic particles could be employed since the present invention, in one embodiment, concerns the use of said materials. Although not believed to be superparamagnetic, crystallites up to 1000 Å can be used with little occurrence of agglomeration. Generally, the more dilute the magnetically-dilute particles are, the more effectively will such particles resist agglomeration.

As explained in the said concurrently-filed application, Ser. No. 29,577 (now U.S. Pat. No. 4,233,168) porous bodies of magnetic glass and crystal-containing material having magnetic crystals therein exhibiting a coercive force of less than 100 oersteds exhibit some agglomeration, but are operable. Crystallites having sizes of less than 500 Å, desirably no more than about 200 Å, and exhibiting coercive forces of less than 40 oersteds, are preferred. The magnetic bodies of said concurrently filed application would be considered magnetically-dilute.

As discussed previously, the preferred matrix is the product resulting from the aforementioned alkali metal-iron-borosilicate base glasses of concurrently-filed Ser. No. 29,577 (now U.S. Pat. No. 4,233,169). As examples of other matrices, there may be mentioned inorganic possibilities such as refractories, and organic polymers such as polymethyl methacrylate, polystyrene, polypropylene, polytetrafluoroethylene, nylon, and acetal copolymer. In addition to magnetite, gamma iron oxide, ferrites such as zinc or cobalt ferrite, and magnetoplumbites such as lead ferrite or barium ferrite, could be used as the magnetic material.

Certainly, when possible, it would be highly desirable to use metallic magnetic crystals which have a stronger magnetism than the ferrites or oxides because less mass of magnetic particles would be needed. Indeed, for superparamagnetism, metallic magnetic particles should be about 50 Å or smaller in size. Such finely-divided metal is so chemically active, however, that it would be extremely difficult to incorporate it in a polymer. On the other hand, Ser. No. 29,577 (now U.S. Pat. No. 4,233,169) supra, discloses a technique for precipitating oxide-type magnetic species from a glass melt and controlling the magnetic crystal size by means of a heat treatment. All of the iron (or other magnetic atom) oxide in the glass-forming batch does not end up as magnetic crystals in the glass. Typically, the magnetic materials used in this invention have a volume fraction of magnetic crystals of less than 20%. Such weakly magnetic particles can be expeditiously separated in a weak magnetic separator positioned external to a liquid in which the particles are suspended.

Whether or not specific magnetic carrier particles are superparamagnetic can easily be determined by applying a magnetic field gradient to them sufficient to hold them, e.g., the pole of a laboratory magnet, and then removing the magnetic field. If, after removal of the field, the individual magnetic particles are free-flowing, that is, do not stick to one another when dispersed into a liquid, the particles are superparamagnetic as that term is used herein.

Different methods of preparation of the magnetic carrier particles will be apparent to the skilled artisan. The magnetic material can be dispersed in an organic polymer matrix during polymer forming and/or working operations. For example, procedures for introducing pigments into polymers can be used. Turning to the inorganics, quite often procedures similar to glass-making are operable. Of course, methods to produce the preferred carrier particle or porous glass and/or crystalline matrix with embedded magnetic material are described in the aforementioned concurrently-filed Ser. No. 29,577 (now U.S. Pat. No. 4,233,169).

The carrier particles will generally have a range of sizes of up to about 4 microns in diameter with a typical size of about 1-2 microns.

In a very preferred embodiment of this invention, the carrier particles are porous. The pores can be continuous or discontinuous as long as they are accessible from the exterior of the individual particles. Various methods can be used to introduce the pores, for example, blowing techniques with organic polymers and the leaching technique described in the aforementioned concurrently-filed Ser. No. 29,577 (now U.S. Pat. No. 4,233,169). The pore size and pore volume can conveniently be the same as those of controlled-pore glass. For example, pore size could average about 350-1000 Å, say about 550 Å, and pore volume could range from about 0.25-1.5 milliliters of pore volume per gram of material, say about 0.7 ml/g. The porous particles, particularly with glass and crystal-containing material, would be characterized by a porous skeleton material with the magnetic material being dispersed throughout the skeleton in a substantially uniform manner.

The carrier particle size and pore characteristics (where a porous substrate is employed) discussed above are not limiting but exemplary only.

In the other broad embodiment of this invention, a magnetically-dilute material (less than 20% by volume of magnetic material in the matrix) is employed which is not superparamagnetic. Although the use of such carrier particles will have the disadvantage that individual carrier particles will exhibit a slight tendency to stick to one another, such materials are operable in SPIA procedures. The tendency to agglomerate will be much less for magnetically-dilute material than for fine particles of normal magnetic material such as $Fe_3O_4$. For example, upon re-dispersion of magnetically-dilute glass or crystal-containing particles into a fluid after removal of a magnetic field, sufficient agitation can be used to maintain good dispersion. The particle size may be of the order discussed above. Preferably, but not necessarily so, the carrier magnetic particles are porous. Preparation of such a material can be carried out using glass-making procedures with selection of glass-forming formulation, together with the use or omission of leaching, depending on whether or not porous particles are to be made.

Although it may be possible to directly form carrier particles of the size desired via the use of some types of matrices, often, and particularly with the inorganics, crushing, possibly with a classification step, will be used.

The following Table sets forth magnetic glass data for some glasses usable in the present invention.

TABLE

Magnetic Data on Some Sample Magnetic Glass Materials

| Sample Number | Saturation Magnetic Moment $M_{sat}$ emu/g | Coercive Force Oersteds, $H_c$ | Remanent Magnetism emu/g | *Volume Fraction Magnetic Crystals | Pore Size Å | Porosity ml/gram |
|---|---|---|---|---|---|---|
| 1 | 10.3 | 9 | — | 0.056 | 300–1800 | 0.30 |
| 2 | 14.4 | 239 | — | 0.084 | Solid | |
| 3 | 6.0 | — | 0.002 | 0.033 | Solid | |
| 4 | 22.6 | — | 6.6 | 0.138 | 500 | 0.30 |
| 5 | 5.55 | — | 0.003 | 0.030 | 2100 | 0.37 |
| 6 | 10.1 | 16 | — | 0.057 | 270 | 0.3 |
| 7 | 6.6 | 9 | — | 0.037 | 500 | 0.5 |

*Estimated from saturation magnetic moment (second column) of the glass sample; assumes a saturation magnetic moment for magnetic crystals per se of 90 emu/g and a magnetic crystal density of 4.8 g/cc. The glass matrix was assumed to have a density of 2.2 grams/cc.

From the standpoint of using the magnetic particles in an SPIA, the procedure followed heretofore is used except for the separation step(s). In place of the widely-used centrifugation, magnetic separation can be carried out. Assuming the use of test tubes, a permanent magnet or an electromagnet is brought into the vicinity of the tubes when separation is to be accomplished. The magnet can be positioned to pull and hold the magnetic particles in any direction; for example, the magnet could be set perpendicular to the long axis of the tube to pull the magnetic particles to one side of the tube. Then, aspiration could be used to remove fluid from the tube. The next fluid is added, the magnetic field is removed and re-dispersion carried out. Obviously, a single magnet of sufficient size can be employed for an array of aligned tubes.

At times caution must be exercised during the separation step to ensure retention of essentially all of the magnetic material. When a weak separator is used with weakly magnetic material, the magnetic material will collect satisfactorily in predetermined limited areas of the containing vessel. However, when the liquid is aspirated or decanted away, there is a tendency for surface tension to pull the wet cake of magnetic material away from the vessel wall and keep the wet cake with the main body of liquid, thereby defeating the separation operation. In such cases a small amount of detergent or surface active material can be introduced to reduce surface tension and restore proper operation of the separation technique. Many immunoassays incorporate such a surfactant within the reagents of the assay. Incorporation of a suitable surfactant is advisable in the design stage of SPIA assays based upon the use of magnetically-dilute particle solid phases and involving weak magnetic separators. This surface tension effect is more significant when the quantity of solid phase used in the assay is small.

Use of the concepts outlined previously enables those skilled in the art of magnetic device design to devise single or multitube separators. Generally, multitube separators will use carefully designed pole pieces with fewer permanent or electromagnets. We have designed a multitube permanent magnet separator, using 2 magnets, approximating the properties of a strong separator. In this separator the minimum field strength in the assay liquid volume is of the order of two kilo-oersteds, ensuring that all magnetic particles are well magnetized. The average field gradient is about 5000 oersteds per centimeter. This separator pulls the particles to a vertical line on the inside surface of the test vessel terminating well clear of the bottom. A compact 14 tube permanent magnet separator approximating the properties of a weak separator has also been designed. The minimum field strength is about 700 oersteds, enough to magnetize the particles to at least half their saturated magnetization. The average field gradient is about 1000 oersteds per centimeter. This separator pulls the particles onto the side walls, even those starting near the bottom. Other schemes and designs can be devised by those skilled in the art.

Shielding means could be employed to remove the magnetic field. Another possibility is to use the magnet to hold the solid carrier in the tube and allow the fluid to flow out of the tube through an orifice. Other separation procedures will be apparent to the skilled artisan.

The biological material, if antigen, hapten, antibody, or enzyme, can be immobilized on the carrier particles using methods known in the art. For example, see U.S. Pat. No. 3,652,761 to Weetall. Absorption, adsorption and covalent bonding may be involved in the coupling step. Also, see the aforementioned Chapter 3 of Immobilized Enzymes for Industrial Reactors, particularly pages 52-53. Surfaces modification techniques for the matrix materials contemplated herein are available.

The examples presented hereinbelow are to illustrate the use of the carrier particles of this invention in SPIA procedures.

EXAMPLE 1

REVERSE SANDWICH IMMUNOASSAY FOR TSH

The "reverse" mode RIA procedure described in U.S. Pat. No. 4,098,876 was carried out for determining TSH. See Example 1 of U.S. Pat. No. 4,098,876. The carrier particles were controlled-pore glass. Thereafter, the assay was repeated using magnetic carrier glass particles designated Sample 1 in the above table, prepared as disclosed in said concurrently-filed Ser. No. 29,577 (now U.S. Pat. No. 4,233,169), and having the following characteristics:
  pore size range—300 to 1800 Å
  pore volume—0.30 ml/g
  particle size—2μ
  saturated magnetic moment—10.3 emu/g
  magnetic moment at 700 oersteds magnetizing field—6.8 emu/g
  coercive force—9 oersteds
  volume percent of magnetic crystals—5.6%

The magnetic glass was prepared to be very close in properties to controlled-pore glass except for the dispersion of the fine magnetic material crystals throughout the glass skeleton, which is mostly silica. Standard immunoassay dose response curves were prepared from both runs as shown in the drawing where the upper curve was obtained with standard controlled-pore glass and the lower curve was obtained with the magnetic controlled-pore glass. Percent bound is plotted along the vertical axis, and micro international units human TSH/ml is plotted along the horizontal axis. It is apparent that the two curves are essentially identical.

EXAMPLE 2

TOTAL T-4 RIA

The Corning Medical IMMO PHASE ™ RIA for total T-4 was performed substituting a non-porous magnetic glass, Sample 2 of the above table, for the controlled-pore glass of the RIA kit, using the procedure described in the kit package insert. Total T-4 values obtained in both runs were in agreement. Magnetic separation was carried out in place of centrifugation with the magnetic carrier particles. As set forth in the Table, Sample 2 glass has a saturation magnetic moment of 14.4 emu/g and about 8.4% by volume is magnetic crystals.

Variations of the invention will be obvious to the skilled artisan.

We claim:

1. In a process for carrying out a solid-phase immunoassay wherein a biological material is complexed with a water-insoluble, inert particulate carrier and, during the assay, the particulate carrier is separated from a fluid, the improvement which comprises utilizing, as said particulate carrier, water-insoluble, inert, magnetically-dilute particles of a glass and/or crystal-containing material having iron-containing, magnetic crystals incorporated therein with dimensions of less than about 1000 Å which are essentially enveloped within the glass and/or crystal structure, and magnetically separating said particulate carrier from said fluid.

2. A process according to claim 1 wherein said biological material is an antigen, a hapten, an enzyme, or an antibody.

3. A process according to claim 1 wherein said glass and/or crystal-containing material consists of a crystalline ceramic.

4. A process according to claim 1 wherein said glass and/or crystal-containing material consists of a glass.

5. A process according to claim 4 wherein said glass has a composition in the alkali metal-iron-borosilicate system.

6. A process according to claim 1 wherein said glass and/or crystal-containing material consists of a crystal-containing material.

7. A process according to claim 1 wherein said magnetic crystals are selected from the group of gamma iron oxide, magnetite, a ferrite, and mixtures thereof.

8. A process according to claim 1 wherein said magnetic crystals constitute less than 20% by volume of said particulate carrier.

9. A process according to claim 1 wherein said water-insoluble, inert, magnetically-dilute particles are porous.

10. A process according to claim 1 wherein said particles consist of a crystalline ceramic.

11. A process according to claim 9 wherein said particles consist of glass.

12. A process according to claim 11 wherein said particles are composed of a porous skeleton consisting essentially of vitreous silica with said magnetic crystals dispersed therewithin.

13. A process according to claim 12 wherein said magnetic crystals constitute less than 20% by volume of said particles.

14. A process according to claim 9 wherein said particles consist of a crystal-containing material.

15. A process according to claim 14 wherein said particles are composed of a glassy crystalline skeleton with said magnetic crystals enveloped therewithin, said glass consisting essentially of vitreous silica and said crystal phase consisting essentially of a silica-containing species.

16. A process according to claim 15 wherein said magnetic crystals constitute less than 20% by volume of said particles.

17. A process according to claim 1 wherein a surfactant is incorporated into said fluid during the separation operation.

18. A solid-phase immunoassay reagent consisting essentially of water-soluble, inert, magnetically-dilute carrier particles having biological material carried on the surface thereof, which particles consist essentially of a glass and/or crystal-containing material having iron-containing, magnetic crystals incorporated therein with dimensions of less than about 1000 Å which are essentially enveloped within the glass and/or crystal structure.

19. A reagent according to claim 18 wherein said biological material is an antigen, a hapten, an enzyme, or an antibody.

20. A reagent according to claim 18 wherein said glass and/or crystal-containing material consists of a crystalline ceramic.

21. A reagent according to claim 18 wherein said glass and/or crystal-containing material consists of a glass.

22. A reagent according to claim 21 wherein said glass has a composition in the alkali metal-iron-borosilicate system.

23. A reagent according to claim 18 wherein said glass and/or crystal-containing material consists of a crystal-containing material.

24. A reagent according to claim 18 wherein said magnetic crystals are selected from the group of gamma iron oxide, magnetite, a ferrite, and mixtures thereof.

25. A reagent according to claim 18 wherein said magnetic crystals constitute less than 20% by volume of said carrier particles.

26. A reagent according to claim 18 wherein said particles are porous.

27. A reagent according to claim 26 wherein said particles consist of a crystalline ceramic.

28. A reagent according to claim 26 wherein said particles consist of glass.

29. A reagent according to claim 28 wherein said particles are composed of a porous skeleton consisting essentially of vitreous silica with said magnetic crystals dispersed therewithin.

30. A reagent according to claim 29 wherein said magnetic crystals constitute less than 20% by volume of said particles.

31. A reagent according to claim 26 wherein said particles consist of a crystal-containing material.

32. A reagent according to claim 31 wherein said particles are composed of a glassy-crystalline skeleton with said magnetic crystals enveloped therewithin, said glass consisting essentially of vitreous silica and said crystal phase consisting essentially of a silica-containing phase.

33. A reagent according to claim 32 wherein said magnetic crystals constitute less than 20% by volume of said particles.

34. A radioimmunoassay kit containing the reagent of claim 18.

* * * * *